US009381371B2

(12) United States Patent
Stubbs et al.

(10) Patent No.: US 9,381,371 B2
(45) Date of Patent: *Jul. 5, 2016

(54) IMPLANTABLE MEDICAL DEVICE WITH AUTOMATIC TACHYCARDIA DETECTION AND CONTROL IN MRI ENVIRONMENTS

(71) Applicant: Cardiac Pacemakers, Inc., St. Paul, MN (US)

(72) Inventors: Scott R. Stubbs, Maple Grove, MN (US); James O. Gilkerson, Stillwater, MN (US); Hiten J. Doshi, Plymouth, MN (US); Diane Schuster, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/058,251

(22) Filed: Oct. 20, 2013

(65) Prior Publication Data
US 2014/0046390 A1 Feb. 13, 2014

Related U.S. Application Data

(63) Continuation of application No. 12/907,517, filed on Oct. 19, 2010, now Pat. No. 8,565,874.

(60) Provisional application No. 61/267,573, filed on Dec. 8, 2009.

(51) Int. Cl.
*A61N 1/37* (2006.01)
*A61N 1/39* (2006.01)
(Continued)

(52) U.S. Cl.
CPC .............. *A61N 1/3962* (2013.01); *A61N 1/056* (2013.01); *A61N 1/37* (2013.01); *A61N 1/3718* (2013.01); *A61N 2001/086* (2013.01)

(58) Field of Classification Search
CPC ...... A61N 1/37; A61N 1/3718; A61N 1/3962; A61N 1/3925; A61N 2001/086; A61B 5/055
See application file for complete search history.

(56) References Cited

U.S. PATENT DOCUMENTS 3,888,260 A 6/1975 Fischell
3,898,995 A 8/1975 Dresbach
(Continued)

FOREIGN PATENT DOCUMENTS

EP 0530006 A1 3/1993
EP 0591334 A1 4/1994
(Continued)

OTHER PUBLICATIONS

"The Gradient System", downloaded from http://www.medical.siemens.com, 1 page.
(Continued)

*Primary Examiner* — Tammie K Heller
(74) *Attorney, Agent, or Firm* — Schwegman Lundberg & Woessner, P.A.

(57) ABSTRACT

An implantable medical device (IMD) includes a lead having one or more sensing electrodes and one or more therapy delivery electrodes, and a sensor configured to detect the presence of static and time-varying scan fields in a magnetic resonance imaging (MRI) environment. A controller, in electrical communication with the lead and the sensor, is configured to process signals related to tachycardia events sensed via the one or more sensing electrodes and to deliver pacing and shock therapy signals via the one or more therapy delivery electrodes. The controller compares the sensed static and time-varying scan fields to static and time-varying scan field thresholds. The controller controls delivery of anti-tachycardia pacing and shock therapy signals as a function of the detected tachycardia events, the comparison of the sensed static scan field to the static scan field threshold, and the comparison of the time-varying scan fields to the time-varying scan field thresholds.

20 Claims, 3 Drawing Sheets

(51) Int. Cl.
*A61N 1/05* (2006.01)
*A61N 1/08* (2006.01)

(56) References Cited

U.S. PATENT DOCUMENTS

| | | |
|---|---|---|
| 4,091,818 A | 5/1978 | Brownlee et al. |
| 4,379,459 A | 4/1983 | Stein |
| 4,404,125 A | 9/1983 | Abolins et al. |
| 4,516,579 A | 5/1985 | Irnich |
| 4,611,127 A | 9/1986 | Ibrahim et al. |
| 4,694,837 A | 9/1987 | Blakeley et al. |
| 4,729,376 A | 3/1988 | DeCote, Jr. |
| 4,751,110 A | 6/1988 | Gulla et al. |
| 4,779,617 A | 10/1988 | Whigham |
| 4,823,075 A | 4/1989 | Alley |
| 4,841,259 A | 6/1989 | Mayer |
| 4,869,970 A | 9/1989 | Gulla et al. |
| 4,934,366 A | 6/1990 | Truex et al. |
| 5,038,785 A | 8/1991 | Blakeley et al. |
| 5,075,039 A | 12/1991 | Goldberg |
| 5,076,841 A | 12/1991 | Chen et al. |
| 5,120,578 A | 6/1992 | Chen et al. |
| 5,181,511 A | 1/1993 | Nickolls et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsitlik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,900 A | 8/1995 | Sundstrom |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,662,697 A | 9/1997 | Li et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,241 A | 7/1998 | Felblinger et al. |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | McCullough et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spehr |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall et al. |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |

(56) References Cited

U.S. PATENT DOCUMENTS

| | | |
|---|---|---|
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,944,489 B2 | 9/2005 | Zeijlemaker et al. |
| 6,963,779 B1 | 11/2005 | Shankar |
| 7,013,180 B2 | 3/2006 | Dublin et al. |
| 7,020,517 B2 | 3/2006 | Weiner |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,801,625 B2 | 9/2010 | MacDonald |
| 7,835,803 B1 | 11/2010 | Malinowski et al. |
| 7,839,146 B2 | 11/2010 | Gray |
| 8,014,867 B2 | 9/2011 | Cooke et al. |
| 8,032,228 B2 | 10/2011 | Ameri et al. |
| 8,086,321 B2 | 12/2011 | Ameri |
| 8,121,705 B2 | 2/2012 | MacDonald |
| 8,160,717 B2 | 4/2012 | Ameri |
| 8,311,637 B2 | 11/2012 | Ameri |
| 8,543,207 B2 | 9/2013 | Cooke et al. |
| 8,554,335 B2 | 10/2013 | Ameri et al. |
| 8,565,874 B2 | 10/2013 | Stubbs et al. |
| 8,571,661 B2 | 10/2013 | Stubbs et al. |
| 8,639,331 B2 | 1/2014 | Stubbs et al. |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton et al. |
| 2002/0166618 A1 | 11/2002 | Wolf et al. |
| 2002/0175782 A1 | 11/2002 | Trinh et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti et al. |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1 | 3/2004 | Larson et al. |
| 2004/0088012 A1 | 5/2004 | Kroll et al. |
| 2004/0093432 A1 | 5/2004 | Luo et al. |
| 2004/0263174 A1 | 12/2004 | Gray et al. |
| 2005/0043761 A1 | 2/2005 | Connelly et al. |
| 2005/0070787 A1 | 3/2005 | Zeijlemaker |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 | 9/2005 | Stevenson |
| 2005/0222656 A1 | 10/2005 | Wahlstrand et al. |

(56) References Cited

U.S. PATENT DOCUMENTS

| | | |
|---|---|---|
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0173295 A1 | 8/2006 | Zeijlemaker |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0019354 A1 | 1/2007 | Kamath |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0154342 A1 | 6/2008 | Digby et al. |
| 2008/0221638 A1 | 9/2008 | Wedan et al. |
| 2008/0234772 A1 | 9/2008 | Shuros et al. |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0157146 A1 | 6/2009 | Linder et al. |
| 2009/0204182 A1 | 8/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |
| 2011/0137359 A1 | 6/2011 | Stubbs et al. |
| 2011/0270338 A1 | 11/2011 | Cooke et al. |
| 2011/0276104 A1 | 11/2011 | Ameri et al. |
| 2012/0071941 A1 | 3/2012 | Ameri |
| 2012/0253425 A1 | 10/2012 | Yoon et al. |
| 2014/0018870 A1 | 1/2014 | Cooke et al. |
| 2014/0046392 A1 | 2/2014 | Stubbs et al. |
| 2014/0135861 A1 | 5/2014 | Stubbs et al. |

FOREIGN PATENT DOCUMENTS

| | | |
|---|---|---|
| EP | 0331959 B1 | 12/1994 |
| EP | 0891786 A2 | 1/1999 |
| EP | 0891207 B1 | 11/1999 |
| EP | 0980105 A1 | 2/2000 |
| EP | 0989623 A1 | 3/2000 |
| EP | 0989624 A1 | 3/2000 |
| EP | 1007132 A2 | 6/2000 |
| EP | 1109180 A2 | 6/2001 |
| EP | 1128764 A1 | 9/2001 |
| EP | 0705621 B1 | 1/2002 |
| EP | 1191556 A2 | 3/2002 |
| EP | 1271579 A2 | 3/2003 |
| EP | 0719570 B1 | 4/2003 |
| EP | 1308971 A2 | 5/2003 |
| EP | 1007140 B1 | 10/2003 |
| EP | 1372782 A2 | 1/2004 |
| EP | 0870517 B1 | 6/2004 |
| EP | 1061849 B1 | 11/2005 |
| EP | 1060762 B1 | 8/2006 |
| EP | 0836413 B1 | 8/2008 |
| WO | WO9104069 A1 | 4/1991 |
| WO | WO9638200 A1 | 12/1996 |
| WO | WO9712645 A1 | 4/1997 |
| WO | WO0054953 A1 | 9/2000 |
| WO | WO0137286 A1 | 5/2001 |
| WO | WO0180940 A1 | 11/2001 |
| WO | WO0186774 A1 | 11/2001 |
| WO | WO02056761 A2 | 7/2002 |
| WO | WO02065895 A2 | 8/2002 |
| WO | WO02072004 A2 | 9/2002 |
| WO | WO02089665 A1 | 11/2002 |
| WO | WO02092161 A1 | 11/2002 |
| WO | WO03013199 A2 | 2/2003 |
| WO | WO03037399 A2 | 5/2003 |
| WO | WO03059445 A2 | 7/2003 |
| WO | WO03061755 A2 | 7/2003 |
| WO | WO03063258 A1 | 7/2003 |
| WO | WO03063952 A2 | 8/2003 |
| WO | WO03063954 A1 | 8/2003 |
| WO | WO03063955 A1 | 8/2003 |
| WO | WO03063956 A2 | 8/2003 |
| WO | WO03063958 A1 | 8/2003 |
| WO | WO03063962 A1 | 8/2003 |
| WO | WO03070098 A2 | 8/2003 |
| WO | WO03073449 A1 | 9/2003 |
| WO | WO03073450 A1 | 9/2003 |
| WO | WO03086538 A1 | 10/2003 |
| WO | WO03090846 A2 | 11/2003 |
| WO | WO03090854 A1 | 11/2003 |
| WO | WO03095022 A2 | 11/2003 |
| WO | WO03063946 A2 | 4/2005 |
| WO | WO2006124481 A2 | 11/2006 |

OTHER PUBLICATIONS

Dempsey Mary F. et al., "Investigation of the Factors Responsible for Burns During MRI", Journal of Magnetic Resonance Imaging 2001;13:627-631.

File History for U.S. Appl. No. 11/015,807, filed Dec. 17, 2004.

Hebrank FX, Gebhardt M. SAFE model: a new method for predicting peripheral nerve stimulations in MRI (abstr) In: Proceedings of the Eighth Meeting of the International Society for Magnetic Resonance in Medicine. Berkeley, Calif: International Society for Magnetic Resonance in Medicine, 2000; 2007.

International Search Report and Written Opinion issued in PCT/US2009/059093, mailed Dec. 29, 2009.

International Search Report and Written Opinion issued in PCT/US2009/068314, mailed Mar. 25, 2009, 14 pages.

International Search Report and Written Opinion issued in PCT/US2010/053202, mailed Dec. 30, 2010, 12 pages.

Kerr, Martha, "Shock Rate Cut 70% With ICDs Programmed to First Deliver Antitachycardia Pacing: Results of the PainFREE Rx II Trial," Medscape CRM News, May 21, 2003.

Luechinger, Roger et al., "In vivo heating of pacemaker leads during magnetic resonance imaging", European Heart Journal 2005;26:376-383.

Nyenhuis, John A. et al., "MRI and Implantable Medical Devices: Basic Interactions With an Emphasis on Heting", IEEE Transactions on Device and Materials Reliability, vol. 5, No. Sep. 2005, pp. 467-480.

Schueler, et al., "MRI Compatibility and Visibility Assessment of Implantable Medical Devices", Journal of Magnetic Resonance Imaging, 9:596-603 (1999).

Shellock FG, "Reference manual for magnetic resonance safety, implants, and devices", pp. 136-139, 2008 ed. Los Angeles; Biomedical Research Publishing Group; 2008.

Shellock, Frank G. et al., "Cardiovascular catheters and accessories: ex vivo testing of ferromagnetism, heating, and artifacts associated with MRI", Journal of Magnetic Resonance Imaging, Nov./Dec. 1998; 8:1338-1342.

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock Therapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology vol. 48, No. 2, 2006. doi:10.1016/j.jacc.2006.03.037.

IMPLANTABLE MEDICAL DEVICE WITH AUTOMATIC TACHYCARDIA DETECTION AND CONTROL IN MRI ENVIRONMENTS

CROSS-REFERENCE TO RELATED APPLICATION

This application is a continuation of U.S. application Ser. No. 12/907,517, filed Oct. 19, 2010, now issued as U.S. Pat. No. 8,565,874, which claims priority to U.S. Provisional Application No. 61/267,573, filed Dec. 8, 2009, which is incorporated herein by reference in its entirety.

TECHNICAL FIELD

The present invention relates to implantable medical devices. In particular, the present invention relates to an implantable medical device with automatic tachycardia detection control in MRI environments.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are various components for implantable medical devices to control delivery of anti-tachycardia pacing and shock therapy signals as a function of detected tachycardia events and sensed static and time-varying MRI scan fields, as well as implantable medical devices including such components and methods related to such implantable medical devices and components.

In Example 1, an implantable medical device (IMD) including a lead having one or more sensing electrodes and one or more therapy delivery electrodes. The IMD also includes a sensor configured to detect the presence of static and time-varying scan fields in a magnetic resonance imaging (MRI) environment. The IMD further includes a controller, in electrical communication with the lead and the sensor, configured to process signals related to tachycardia events sensed via the one or more sensing electrodes and to deliver pacing and shock therapy signals via the one or more therapy delivery electrodes. The controller is also configured to compare the sensed static and time-varying scan fields to static and time-varying scan field thresholds. The controller controls delivery of anti-tachycardia pacing and shock therapy signals as a function of the detected tachycardia events, the comparison of the sensed static scan field to the static scan field threshold, and the comparison of the time-varying scan fields to the time-varying scan field thresholds.

In Example 2, the IMD according to Example 1, wherein the controller disqualifies the tachycardia events to inhibit delivery of the anti-tachycardia pacing and shock therapy signals when the static and time-varying scan field thresholds are exceeded.

In Example 3, the IMD according to either Example 1 or 2, wherein the controller processes sensed tachycardia events, enables delivery of the anti-tachycardia pacing signals, and inhibits delivery of the shock therapy signals when the static scan field threshold is exceeded and the time-varying scan field thresholds are not exceeded.

In Example 4, the IMD according to any of Examples 1-3, wherein the controller processes sensed tachycardia events and enables delivery of the anti-tachycardia pacing and shock therapy signals when the neither of the static and time-varying scan field thresholds is exceeded.

In Example 5, the IMD according to any of Examples 1-4, wherein the controller is operable to switch the IMD between a normal mode and an MRI mode, and wherein the sensor is disabled in the normal mode and the sensor is enabled in the MRI mode.

In Example 6, the IMD according to any of Examples 1-5, wherein the controller automatically switches the IMD from the MRI mode to the normal mode when the static scan field is less than the static scan field threshold.

In Example 7, the IMD according to any of Examples 1-6, wherein the controller further controls delivery of anti-tachycardia pacing and shock therapy signals as a function of programmed therapy settings.

According to Example 8, a method for operating an implantable medical device (IMD) includes sensing static and time-varying scan fields in a magnetic resonance imaging (MRI) environment and comparing the sensed fields to static and time-varying scan field thresholds. Signals related to tachycardia events are detected, and delivery of anti-tachycardia pacing and shock therapy signals is controlled as a function of the detected tachycardia events, the comparison of the sensed state electromagnetic field to the static scan field threshold, and the comparison of the time-varying scan fields to the time-varying scan field thresholds.

In Example 9, the method according to Example 8, wherein the controlling step comprises delivering anti-tachycardia pacing and/or shock therapy signals when a tachycardia event is detected and neither of the static and time-varying scan field thresholds is exceeded.

In Example 10, the method according to either Example 8 or 9, wherein the controlling step comprises delivering the anti-tachycardia pacing signals and inhibiting delivery of the shock therapy signals when signals related to a tachycardia event is detected and the static scan field threshold is exceeded and the time-varying scan field thresholds are not exceeded.

In Example 11, the method according to any of Examples 8-10, wherein the controlling step comprises inhibiting delivery of the anti-tachycardia pacing and shock therapy signals and disqualifying detected tachycardia events when the static and time-varying scan field thresholds are exceeded.

In Example 12, the method according to any of Examples 8-11, wherein the controlling step further comprises controlling delivery of anti-tachycardia pacing and shock therapy signals as a function of programmed therapy settings.

In Example 13, the method according to any of Examples 8-12, wherein, prior to the sensing step, the method further comprises switching the IMD from a normal mode to an MRI mode.

In Example 14, the method according to any of Examples 8-13, and further comprising automatically switching the IMD from the MRI mode to the normal mode when the static scan field is less than the static scan field threshold.

According to Example 15, a method for operating an implantable medical device (IMD) includes sensing static and time-varying scan fields in a magnetic resonance imaging (MRI) environment and comparing the sensed fields to static and time-varying scan field thresholds. Signals related to tachycardia events are detected, and delivery of anti-tachycardia pacing and shock therapy signals is controlled as a function of the detected tachycardia events and the threshold comparisons. Particularly, anti-tachycardia pacing and/or shock therapy signals are delivered when a tachycardia event is detected and neither of the static and time-varying scan field thresholds is exceeded. In addition, the anti-tachycardia pacing signals are delivered and delivery of the shock therapy signals is inhibited when signals related to a tachycardia event is detected and the static scan field threshold is exceeded and the time-varying scan field thresholds are not exceeded. Furthermore, delivery of the anti-tachycardia pacing and shock therapy signals is inhibited and detected tachycardia events are disqualified when the static and time-varying scan field thresholds are exceeded.

In Example 16, the method according to Example 15, wherein, prior to the sensing step, the method further comprises switching the IMD from a normal mode to an MRI mode.

In Example 17, the method according to either Example 16 or 17, and further comprising automatically switching the IMD from the MRI mode to the normal mode when the static scan field is less than the static scan field threshold.

In Example 18, the method according to any of Examples 15-17, wherein the controlling step further comprises controlling delivery of anti-tachycardia pacing and shock therapy signals as a function of programmed therapy settings.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
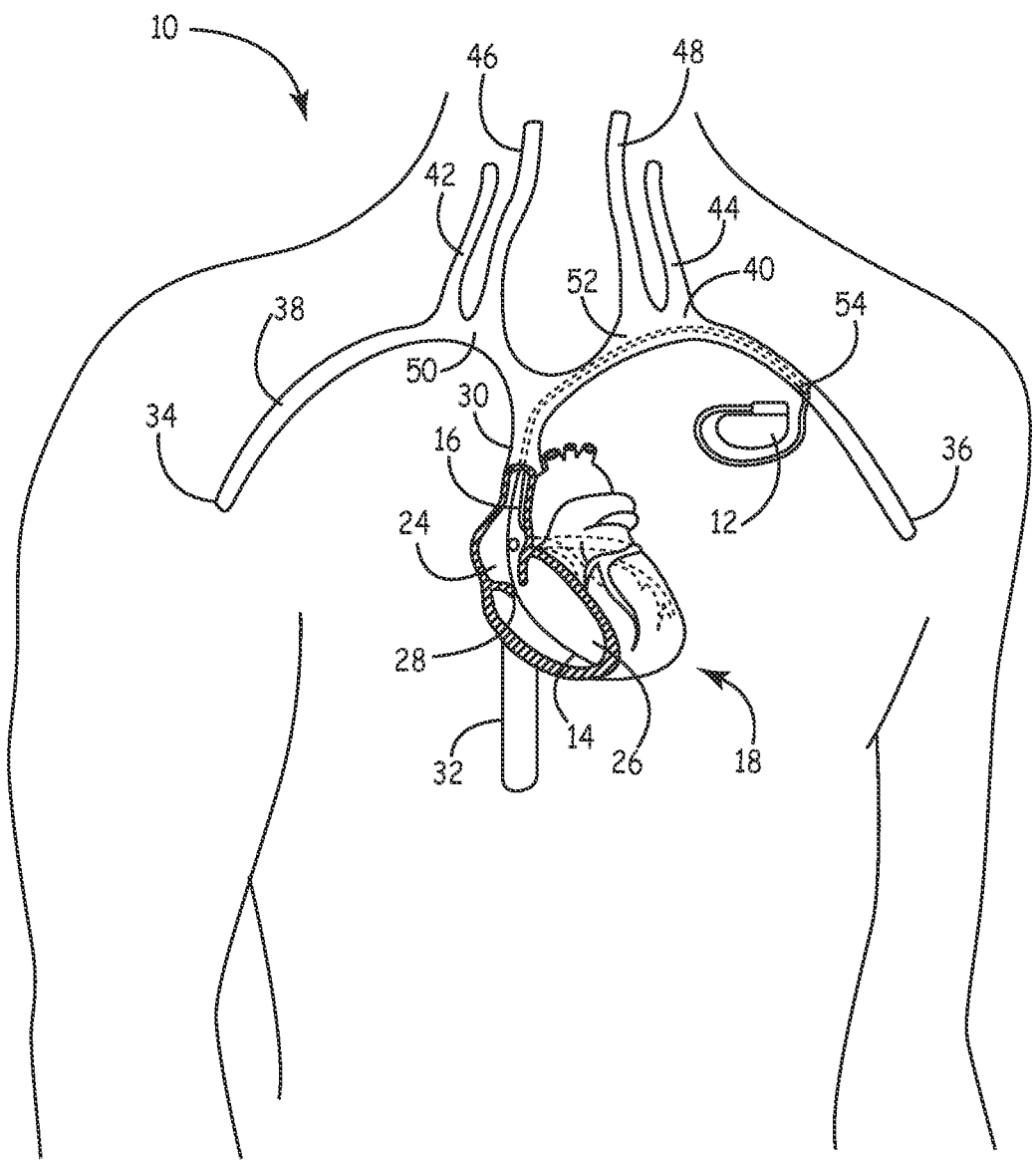
FIG. 1 is a schematic view of a cardiac rhythm management (CRM) system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management (CRM) system 10 according to an embodiment of the present invention. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey electrical signals and stimuli between the heart 18 and the pulse generator 12. In the illustrated embodiment, the lead 14 is implanted in the right ventricle 26, and the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy system. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In other embodiments of the present invention, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

Figure 2:
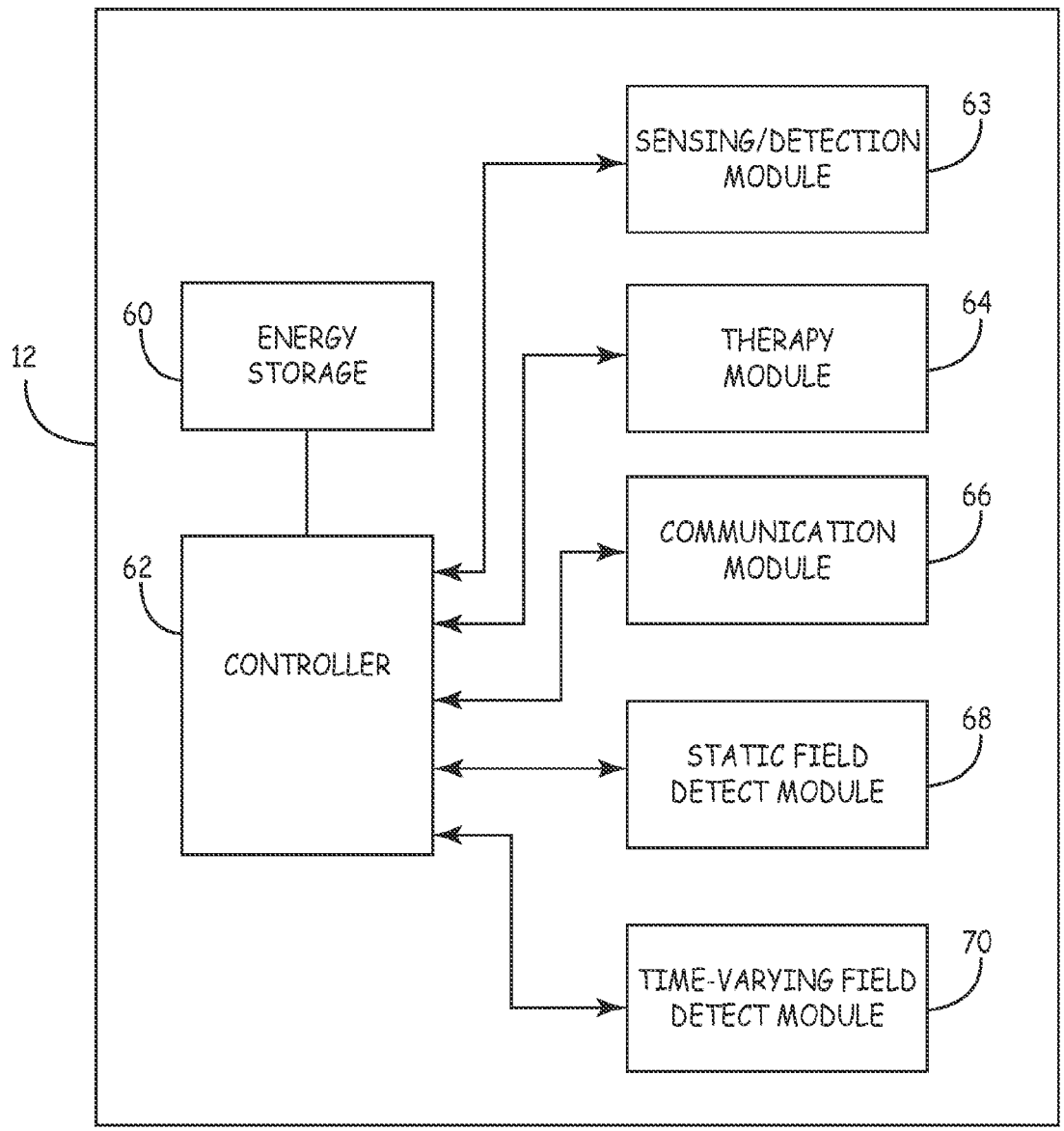
FIG. 2 is a functional block diagram of an implantable medical device (IMD) configured to detect fields generated by magnetic resonance imaging (MRI) systems and deliver anti-tachycardia therapy as a function of the detected fields.

FIG. 2 is a functional block diagram of an embodiment of the IMD 12. The IMD 12 includes an energy storage device 60, a controller 62, a sensing and detection module 63, a therapy module 64, a communication module 66, a static field detect module 68, and a time-varying field detect module 70. The term "module" is not intended to imply any particular structure. Rather, "module" may mean components and circuitry integrated into a single unit as well as individual, discrete components and circuitry that are functionally related. In addition, it should be noted that IMD 12 may include additional functional modules that are operable to perform other functions associated with operation of IMD 12.

The energy storage device 60 operates to provide operating power to the controller 62, sensing and detection module 63, therapy module 64, communication module 66, static field detect module 68, and time-varying field detect module 70. The controller 62 operates to control and receive signals from the sensing and detection module 63, therapy module 64, communication module 66, static field detect module 68, and time-varying field detect module 70, each of which is operatively coupled to and communicates with the controller 62. For example, the controller 62 may command the therapy module 64 to deliver a desired therapy, such as a pacing or defibrillation stimulus, based on signals received from the sensing and detection module 63. In addition, the controller 62 may command the communication module 66 to transmit and/or receive data from an external device (e.g., a programmer). Furthermore, the controller 62 may receive signals from the static field detect module 68 and/or the time-varying field detect module 70 indicating the presence or absence of fields generated by an MRI scan.

The IMD 12 may also include timing circuitry (not shown) which operates to schedule, prompt, and/or activate the IMD 12 to perform various activities. In one embodiment, the timing circuitry is an internal timer or oscillator, while in other embodiments, timing may be performed by specific hardware components that contain hardwired logic for performing the steps, or by any combination of programmed computer components and custom hardware components.

The communication module 66 is configured to both transmit and receive telemetry signals to and from other devices, such as an external programmer. For example, the communication module 66 may be configured to receive signals from the external programmer to switch the operation mode of the communication module 66 between a normal mode and a magnetic resonance imaging (MRI) mode. The IMD 12 may alternatively include at least one transducer configured for receiving a telemetry signal and at least one transducer for transmitting a telemetry signal. The communication module 66 may be any type of device capable of sending and/or receiving information via a telemetry signal, including, but not limited to, a radio frequency (RF) transmitter, an acoustic transducer, or an inductive transducer.

The sensing and detection module 63 and therapy module 64 operate to perform the therapeutic and/or diagnostic functions of the IMD 12. In some embodiments, the sensing and detection module 63 senses signals related to tachycardia events (e.g., tachyarrhythmia) via one or more sensing electrodes on the lead 14, 16. The sensing and detection module 63 may also be operable to automatically determine the capture threshold of the heart 18 by providing a pacing stimulus to the heart 18 and sensing whether the stimulus results in a contraction of the heart 18. One example circuit arrangement that may be included in the sensing and detection module 63 to determine the capture threshold of heart 18 is disclosed in U.S. Pat. No. 7,092,756, entitled "Autocapture Pacing/Sensing Configuration," which is incorporated herein by reference in its entirety.

In some embodiments, the therapy module 64 delivers a cardiac pacing and/or defibrillation stimulus to the heart 18 via one or more therapy electrodes on the lead 14, 16. The type and timing of therapy delivered by the therapy module 64 may be controlled by the controller 62. In some embodiments, the therapy delivery is based on sensed static and time-varying fields, as will be described in more detail below. In addition, the controller 62 may control operation of the therapy module 64 based on programmed therapy settings. The therapy module 64 is not limited to performing any particular type of physiologic therapy, and may be configured to perform other types of physiologic therapy, such as neurological measurements and therapy.

The static field detect module 68 senses the presence of the static magnetic fields associated with an MRI scan. In some embodiments, the static field detect module 68 includes a power inductor and a core saturation detector. When the power inductor saturates in the presence of a static MRI field, the inductance of the power inductor decreases, which is detected by the core saturation detector. One example module having such a configuration that is suitable for use in static field detect module 68 is disclosed in U.S. Pat. No. 7,509,167, entitled "MRI Detector for Implantable Medical Device," which is incorporated herein by reference in its entirety. Any type of sensor or device may alternatively or additionally be incorporated into the static field detect module 68 that is operable to detect the presence of static MRI fields.

The time-varying field detect module 70 senses the presence of the time-varying gradient magnetic fields and radio frequency (RF) electromagnetic fields associated with an MRI scan. The time-varying field detect module 70 may include a magnetometer or other device employable to detect the gradient field dB/dt (i.e., the time derivative of magnetic field B). In some embodiments, the magnetometer includes a Hall effect sensor, a magnetotransistor, a magnetodiode, a magneto-optical sensor, and/or a giant magnetoresistive sensor. The time-varying field detect module 70 may also include an electromagnetic sensor capable of detecting the presence of RF fields. For example, the time-varying field detect module 70 may include an electromagnetic interference (EMI) detector such as that described in U.S. Pat. No. 5,697,958, entitled "Electromagnetic Noise Detector for Implantable Medical Devices," which is herein incorporated by reference in its entirety.

According to some embodiments, the IMD 12 is configured to detect magnetic and electromagnetic fields generated by an MRI system and to control delivery of anti-tachycardia therapy from the therapy module 64 as a function of the detected fields. In particular, the IMD 12 detects the presence of the static and/or time-varying fields associated with an MRI procedure and automatically adjusts the types of therapy delivered to the heart 18 at various levels of MRI influence. This reduces the amount of power drawn from the energy storage device 60 due to failed shock therapy attempts when the IMD 12 is under high static field influence and avoids having to manually disable and enable different types of anti-tachycardia therapy before and after the MRI procedure.

Figure 3:
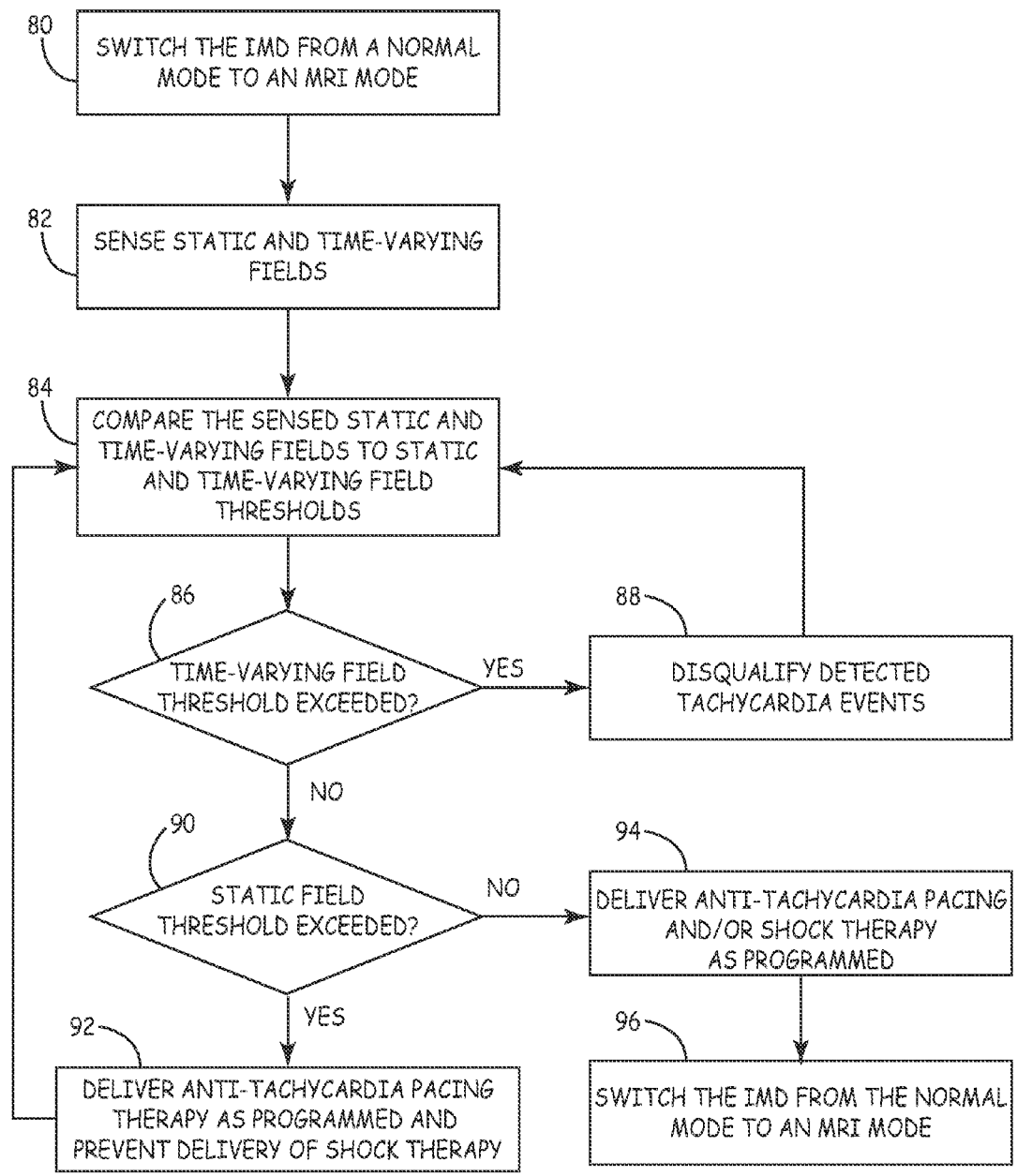
FIG. 3 is a flow diagram of a process for detecting MRI scan fields and controlling delivery of anti-tachycardia therapy as a function of the detected fields.

FIG. 3 is a flow diagram of an exemplary process that may be employed by the IMD 12 to detect the fields generated by an MRI system and control delivery of anti-tachycardia therapy based on the detected fields. At step 80, the IMD 12 is switched from a normal mode of operation to an MRI mode of operation. The IMD 12 may be programmed into the MRI mode by wirelessly sending a signal from an external programmer to the controller 62 via the communication module 66, for example. In some embodiments, the field detect modules 68 and 70 are active in both the normal mode and the MRI mode of operation. In other embodiments, switching the IMD 12 to the MRI mode activates the field detect modules 68 and 70 for detection of MRI scan fields.

The normal operational mode is the operational mode of the IMD 12 as initially programmed. The MRI operational mode can refer to any operational mode of the IMD 12 that is a safe operational mode in the presence of EMI. For example, for a bradycardia engine in a tachycardia device, an MRI mode might be a fixed-rate and/or non-demand (or asynchronous) pacing mode as opposed to a rate-responsive and/or demand pacing mode. In some embodiments, an MRI mode can be both a non-demand mode (i.e., VOO) and a non-rate-responsive mode. Thus, in accordance with one embodiment, switching the IMD 12 to an MRI mode might entail switching the bradycardia engine to a VOO, AOO or DOO pacing mode. The mode to which the device is switched may depend on the original programmed mode of the device. For example, an IMD 12, which is normally programmed to a Dxx mode (i.e., DDDR, DDD, DDI, or DVI) would switch to DOO when in MRI the MRI mode. Similarly, a device programmed to Vxx mode would switch to VOO, and a device programmed to Axx mode would switch to AOO mode.

It should be noted that there may be other modes of operation that are considered safe in an MRI environment, so the present invention is not limited to the MRI modes discussed herein. Further, as one skilled in the art will appreciate, other types of IMDs will have different mode types that might be considered safe in an MRI environment, and those modes also are considered MRI modes for purposes of the present invention.

It should also be noted that step 80 applies to IMDs 12 that are programmed with an MRI mode. In embodiments in which the IMD 12 does not include an MRI mode, the IMD 12 may be configured such that the static field detect module 68 and the time-varying field detect module 70 are maintained in an enabled state such that the presence of static and/or time-varying fields would be detected without being programmed into an MRI mode.

At step 82, the static field detect module 68 detects the presence of static magnetic fields associated with an MRI procedure, and the time-varying field detect module 70 detects the presence of time-varying magnetic and electromagnetic fields associated with an MRI procedure. The step 82 is continuously performed throughout the process illustrated in FIG. 4. That is, the static and time-varying fields are continuously monitored such that the IMD 12 can continuously respond to the changing presence or absence of each of the fields. In some embodiments, the static field detect module 68 and time-varying field detect module 70 provide signals to the controller 62 related to the magnitude of the detected fields. The controller 62 may determine the magnitude of the gradient field by calculating the mean of dB/dt. In some embodiments, the time-varying field detect module 70 also provides signals to controller 62 related to other characteristics of the detected field, such as field frequency and the slew rate of the gradient magnetic field.

After detecting the presence of static and/or time-varying fields, then, at step 84, the controller 62 compares the sensed static and time-varying fields to static and time-varying field thresholds, respectively. The static and time-varying field thresholds may be stored or programmed in the controller 62. The time-varying field threshold may include a magnetic component for the gradient field and an electromagnetic component for the RF field. In some embodiments, the static and time-varying field thresholds are set based on common or expected magnetic and electromagnetic field levels in an MRI environment. This differentiates fields generated by an MRI system from those generated by other sources of magnetic and electromagnetic fields. In one exemplary embodiment, the static field threshold is about 0.2 T, and the gradient field component of the time-varying field threshold is about 10 T/s. The RF component of the time-varying field threshold may be a function of the presence of an RF field associated with an MRI procedure (e.g., 63.864 MHz or 127.728 MHz) in combination with the presence of an electric field having a threshold magnitude.

In decision step 86, if the time-varying field or fields detected by the time-varying field detect module 70 exceed the time-varying field threshold, then, in step 88, the IMD 12 disqualifies tachycardia events detected by the one or more sensing electrodes on the leads 14, 16. The presence of high time-varying fields indicates that an the IMD 12 is being subjected to an active MRI scan. The time-varying fields can induce a current on the leads 14, 16, which may cause the one or more sensing electrodes to incorrectly detect the occurrence of a tachycardia event. Consequently, when time-varying fields that exceed the time-varying threshold are detected, the IMD 12 disqualifies the tachycardia events detected by the sensing and detection module 63 as being unreliable. The process then returns to step 84 to compare the detected fields to the field thresholds.

If, in decision step 86, the time-varying fields detected by the time-varying field detect module 70 do not exceed the time-varying field threshold, then, in decision step 90, the controller 62 determines whether the static field detected by the static field detect module 68 exceeds the static field threshold. If the static field threshold is exceeded, then, in step 92, the controller 62 delivers anti-tachycardia pacing (ATP) therapy as programmed via one or more therapy delivery electrodes on leads 14, 16, but inhibits delivery of shock therapy through the leads 14, 16. The ATP therapy is delivered because tachycardia events detected by the leads in the absence of strong time-varying fields are reliable, and the static fields do not have a substantial effect on the delivery of the ATP therapy. However, in alternative embodiments, the controller 62 may be programmed to disable ATP therapy in the presence of a static field that exceeds the static field threshold. The ATP therapy delivery program may also be selected or changed by a clinician by communicating with the controller 62 via the communication module 66.

Delivery of shock therapy is inhibited in the presence of a strong static field because the strong field may saturate materials associated with the power components of the IMD 12 (e.g., inductors in the energy storage device 60). Under saturation conditions, the time to charge the high voltage capacitor(s) to maximum energy can be protracted, or the maximum energy may not be attainable. Consequently, in order to prevent delayed or failed delivery of the shock therapy, the controller 62 inhibits delivery of shock therapy in the presence of a static field that exceeds the static field threshold.

If the static field threshold is not exceeded in step 90, then, in step 94, the controller 62 delivers ATP and/or shock therapy as programmed when tachycardia events are detected by the one or more sensing electrodes. Thus, the controller 62 adjusts delivery of ATP and/or shock therapy automatically based on the type and magnitude of fields detected by the field detector modules 68, 70. This assures that safe and reliable anti-tachycardia therapy is provided to the patient for the maximum amount of time when the patient is subjected to MRI fields.

In embodiments of the IMD 12 that includes an MRI mode of operation, the IMD 12 may subsequently return to the normal mode of operation, in step 96. In some embodiments, the controller 62 automatically switches the IMD 12 to the normal mode of operation when the detected static field falls below the static field threshold. In alternative embodiments, the static field threshold at which the IMD 12 returns to the normal mode of operation is different than the static field threshold discussed above with regard to decision step 90. The switch to the normal mode of operation may also be further triggered by the detection of a tachycardia event after the static field drops below a threshold level.

In summary, embodiments of the present invention relate to an implantable medical device (IMD) including a lead having one or more sensing electrodes and one or more therapy delivery electrodes. The IMD also includes a sensor configured to detect the presence of static and time-varying scan fields in a magnetic resonance imaging (MRI) environment. The IMD further includes a controller, in electrical communication with the lead and the sensor, configured to process signals related to tachycardia events sensed via the one or more sensing electrodes and to deliver pacing and shock therapy signals via the one or more therapy delivery electrodes. The controller is also configured to compare the sensed static and time-varying scan fields to static and time-varying scan field thresholds. The controller controls delivery of anti-tachycardia pacing and shock therapy signals as a function of the detected tachycardia events, the comparison of the sensed static scan field to the static scan field threshold, and the comparison of the time-varying scan fields to the time-varying scan field thresholds. An IMD having this configuration controls the type of anti-tachycardia therapy delivered to the patient at various levels of MRI influence, reduces the power draw on the IMD battery due to failed shock therapy attempts, and avoids having to manually disable and enable anti-tachycardia therapy before and after the MRI procedure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device (IMD) comprising:
    one or more leads configured to sense cardiac signals and deliver therapy signals;
    a sensor configured to detect the presence of static and time-varying scan fields in a magnetic resonance imaging (MRI) environment; and
    a controller configured to process detect cardiac event based on the cardiac signals, compare the sensed static and time-varying scan fields to static and time-varying scan field thresholds, and control delivery of a first type of stimulation therapy and a second type of stimulation therapy as a function of the detection of the cardiac events, the comparison of the sensed static scan field to the static scan field threshold, and the comparison of the time-varying scan fields to the time-varying scan field thresholds such that:
        when the static and time-varying scan field thresholds are exceeded, the controller disqualifies the cardiac events to inhibit delivery of the first type of stimulation therapy and the second type of stimulation therapy, and
        when the static scan field threshold is exceeded and the time-varying scan field threshold is not exceeded, the controller processes sensed cardiac events, causes the IMD to deliver the first type of stimulation therapy upon detection of the cardiac events, and inhibits delivery of the second type of stimulation therapy.

2. The IMD of claim 1, wherein the first type of stimulation therapy is a pacing therapy.

3. The IMD of claim 2, wherein the second type of therapy is a shock therapy.

4. The IMD of claim 1, wherein the cardiac events comprise tachycardia events.

5. The IMD of claim 1, wherein the controller processes sensed cardiac events and enables delivery of the first type of stimulation therapy and the second type of stimulation therapy when neither of the static and time-varying scan field thresholds are exceeded.

6. The IMD of claim 1, wherein the controller is operable to switch the IMD between a normal mode and an MRI mode, and wherein the sensor is disabled in the normal mode and the sensor is enabled in the MRI mode.

7. The IMD of claim 1, wherein the controller further controls delivery of the first type of stimulation therapy and the second type of stimulation therapy as a function of programmed therapy settings.

8. A method for operating an implantable medical device (IMD), the method comprising:
    sensing for static and time-varying scan fields associated with a magnetic resonance imaging (MRI) environment;
    comparing the sensed static and time-varying scan fields to static and time-varying scan field thresholds;
    detecting cardiac events; and
    controlling delivery of a first type of stimulation therapy and a second type of stimulation therapy as a function of the detected cardiac events, the comparison of the sensed state electromagnetic field to the static scan field threshold, and the comparison of the time-varying scan fields to the time-varying scan field thresholds,
    wherein the controlling step comprises causing the IMD to deliver the first type of stimulation therapy and inhibiting the second type of stimulation therapy when a cardiac event is detected, the static scan field threshold is exceeded, and the time-varying scan field threshold is not exceeded, and
    wherein the controlling step comprises inhibiting delivery of both of the first type of stimulation therapy and the second type of stimulation therapy when both of the static and time-varying scan field thresholds are exceeded.

9. The IMD of claim 8, wherein the first type of stimulation therapy is a pacing therapy.

10. The IMD of claim 9, wherein the second type of therapy is a shock therapy.

11. The IMD of claim 8, wherein the cardiac events comprise tachycardia events.

12. The method of claim 8, wherein the controlling step comprises:
    causing the IMD to deliver both of the first type of stimulation therapy and the second type of stimulation therapy when neither of the static and time-varying scan field thresholds is exceeded.

13. The method of claim 8, wherein the controlling step of inhibiting delivery of both of the first type of stimulation therapy and the second type of stimulation therapy when both of the static and time-varying scan field thresholds are exceeded comprises disqualifying detected cardiac events to inhibit the first type of stimulation therapy and the second type of stimulation therapy from being delivered.

14. The method of claim 8, wherein the controlling step further comprises controlling delivery of the first type of stimulation therapy and the second type of stimulation therapy as a function of programmed therapy settings.

15. The method of claim 8, wherein, prior to the sensing step, the method further comprises:
    switching the IMD from a normal mode to an MRI mode.

16. An implantable medical device (IMD) comprising:
    one or more leads configured to sense cardiac signals and deliver therapy signals;

a sensor configured to detect the presence of static and time-varying scan fields in a magnetic resonance imaging (MRI) environment; and a controller configured to detect cardiac events based on the cardiac signals, compare the sensed static and time-varying scan fields to static and time-varying scan field thresholds, and control delivery of a first type of stimulation therapy and a second type of stimulation therapy as a function of the detection of the cardiac events, the comparison of the sensed static scan field to the static scan field threshold, and the comparison of the time-varying scan fields to the time-varying scan field thresholds such that:

when the static and time-varying scan field thresholds are exceeded, the first type of stimulation therapy and the second type of stimulation therapy are both inhibited, and when the static scan field threshold is exceeded and the time-varying scan field threshold is not exceeded, the second type of stimulation therapy is inhibited and the first type of stimulation therapy is delivered based on detection of the cardiac events.

17. The IMD of claim 16, wherein the first type of stimulation therapy is a pacing therapy.

18. The IMD of claim 17, wherein the second type of therapy is a shock therapy.

19. The IMD of claim 16, wherein the cardiac events comprise tachycardia events.

20. The IMD of claim 16, wherein the controller enables delivery of the first type of stimulation therapy and the second type of stimulation therapy when neither of the static and time-varying scan field thresholds are exceeded.

* * * * *